(12) United States Patent
Slocik et al.

(10) Patent No.: US 11,382,976 B1
(45) Date of Patent: *Jul. 12, 2022

(54) ULTRA-STABLE PROTEIN IONIC LIQUIDS

(71) Applicant: Government of the United States, as represented by the Secretary of the Air Force, Wright-Patterson AFB, OH (US)

(72) Inventors: Joseph M Slocik, Dayton, OH (US); Rajesh R. Naik, Centerville, OH (US); Patrick B Dennis, Cincinnati, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 258 days.

This patent is subject to a terminal disclaimer.

(21) Appl. No.: 16/587,092

(22) Filed: Sep. 30, 2019

Related U.S. Application Data

(63) Continuation-in-part of application No. 15/440,832, filed on Feb. 23, 2017, now Pat. No. 10,463,733.

(60) Provisional application No. 62/403,774, filed on Oct. 4, 2016.

(51) Int. Cl.
*A61K 39/395* (2006.01)
*C07K 16/34* (2006.01)
*G01N 33/531* (2006.01)

(52) U.S. Cl.
CPC ........ *A61K 39/39591* (2013.01); *C07K 16/34* (2013.01); *G01N 33/531* (2013.01); *C07K 2317/40* (2013.01); *C07K 2317/94* (2013.01)

(58) Field of Classification Search
CPC .............. A61K 39/39591; C07K 16/34; C07K 2317/40; C07K 2317/94; G01N 33/531
See application file for complete search history.

(56) References Cited

U.S. PATENT DOCUMENTS 10,463,733 B1 * 11/2019 Slocik ................... C08G 65/00
11,058,770 B1 * 7/2021 Slocik ................... C07K 16/00
2003/0211531 A1 * 11/2003 Hampton ............. C12Q 1/6886
435/6.14

FOREIGN PATENT DOCUMENTS

WO  WO-2014055936 A1 *  4/2014  ............. A01N 1/021
WO  2015038811           3/2015
WO  2017070364           4/2017

OTHER PUBLICATIONS

Patel et al., Appl. Biochem Biotechnol 172: 3701-3720 (Year: 2014).*
Lloyd et al. Protein Engineering, Design & Selection 22:159-168 (Year: 2009).*
Edwards et al., J Mol Biol. 334(1): 103-118 (Year: 2003).*
Rudikoff et al., Proc Natl Acad Sci USA vol. 79 pp. 1979-1983 (Year: 1982).*
Brogan, P.S., Enzyme Activity in Liquid Lipase Melts as a Step Towards Solvent-Free Biology at 150C, Nature Communications, DOI: 10.1038/ncomms6058 (2014).
Perriman, Solvent-Free Protein Liquids and Liquid Crystals, Chem. Int. Ed., 2009, 48, 6242-6246.

* cited by examiner

*Primary Examiner* — Phuong Huynh
(74) *Attorney, Agent, or Firm* — AFMCLO/JAZ; Timothy M. Barlow

(57) ABSTRACT

A method comprising: providing aqueous antibodies; cationizing the aqueous antibodies by the addition of stoichiometric amounts of an excess of a positively-charged crosslinker in the presence of a coupling reagent; titrating the cationized antibodies with a counter anionic polymer until the antibody cation/anion pair solution becomes negative by zeta potential measurement, to create at least one antibody cation/anion pair in aqueous solution. The antibodies are one of anti-hemoglobin antibodies, anti-horse spleen ferritin IgG antibodies, or blood-typing IgM Anti-A antibodies, single-chain antibodies from camelids, monoclonal Anti-Flag antibodies, monoclonal Anti-HRP2 to *Plasmodium falciparum*, polyclonal Anti-neuropeptide Y, and polyclonal Anti-human troponin. The antibody cation/anion pair solution may be lyophilized to remove all of the water, forming a lyophilized solid, and the lyophilized solid may be heated to generate an antibody ionic liquid.

12 Claims, 7 Drawing Sheets

ULTRA-STABLE PROTEIN IONIC LIQUIDS

Pursuant to 37 C.F.R. § 1.78(a)(4), this application claims the benefit of and priority to prior filed Provisional Application Ser. No. 62/403,774, filed 4 Oct. 2016, co-pending U.S. patent application Ser. No. 15/440,832, filed 23 Feb. 2017, now U.S. Pat. No. 10,463,733, which are expressly incorporated herein by reference.

RIGHTS OF THE GOVERNMENT

The invention described herein may be manufactured and used by or for the Government of the United States for all governmental purposes without the payment of any royalty.

FIELD OF THE INVENTION

The present invention relates generally to ultra-stable, water-free biological materials and, more particularly, to ultra-stable, heat-resistant, biologically active, water-free antibody ionic liquids that do not require refrigeration.

BACKGROUND OF THE INVENTION

Most biological materials (i.e. proteins and antibodies) thrive in aqueous environments and physiological conditions (neutral pH—between 6-8, ambient temperatures 25-37° C.) in order to perform their biological function. Water is used for stabilizing some biomolecular structures through hydrogen bonding, providing proton donors/acceptors, regulating binding interactions, and controlling molecular dynamics. Conversely, water is also detrimental to biomolecular structure and function by increasing the rate of hydrolysis and oxidation, destabilizing the protein structure, and increasing the susceptibility/sensitivity to elevated temperatures. In total, this results in denaturation, proteolytic degradation, decomposition, and short shelf-lives of these materials.

In order to counteract the effects of water and limit decomposition, current biomolecules, e.g. proteins and antibodies, may require constant refrigeration during storage, handling, and transport in order to preserve their structure, functionality, and biological activity. Generally, antibodies in water may be stable for up to one month when stored at about 4° C. and up to one year when stored in 25% glycerol at −20° C. However, the presence of water in a biological solution will typically result in hydrolysis, even if the temperature is reduced or the solution is frozen. Water promotes hydrogen bonding, intramolecular interactions, stabilizes the antibody structure, facilitates mass transport and diffusion of products, and regulates binding interactions. Water also increases the sensitivity of the antibodies to elevated temperatures, destabilizes protein structures, increases hydrolysis and oxidation rates, reduces shelf lives, and promotes unfolding/denaturation. Consequently, the exclusion of water from antibody preparations is highly appealing and offers a means towards reducing protein degradation, increasing stability, enabling refrigeration-free storage and handling, and significantly increasing shelf-lives. In addition, even if freezing or refrigeration are acceptable alternatives, many places around the world have no available electricity to power refrigeration equipment. The half-life of unrefrigerated antibodies may be as short as 2 days.

SUMMARY OF THE INVENTION

The present invention overcomes the foregoing problems and other shortcomings, drawbacks, and challenges of making stable biologically-active materials, such as proteins and antibodies. While the invention will be described in connection with certain embodiments, it will be understood that the invention is not limited to these embodiments. To the contrary, this invention includes all alternatives, modifications, and equivalents as may be included within the spirit and scope of the present invention.

Based on the numerous drawbacks associated with water in antibody solutions, see above, the aim of this invention, in one embodiment, is the removal of most or all water, i.e. at least 95% water removed, without disrupting the protein/antibody structure and intramolecular interactions/functions. The proteins and/or antibodies are chemically modified into an ionic liquid, but when antibodies are used the modified antibodies maintain high antigen recognition, specificity, and binding affinity, e.g., the modified antibodies maintain picomolar (pM) dissociation constants (KD) about equal to those of native, unmodified antibodies. With regard to binding affinity, this means that the antigens bind strongly to the modified antibodies.

"Water-free" (as defined herein) protein liquids feature the simplicity of traditional inorganic ionic liquids (facile synthesis, ability to tune properties through choice of cation and anion pair, and stability), but display the complexity and functionality of highly active proteins, e.g. antibodies. Because the protein liquids have most or all of the water removed, they are stable liquids, resistant to extreme temperatures (e.g. >100° C.), able to maintain biological recognition activity, and exhibit much longer shelf-lives without the need for refrigeration.

According to one embodiment of the present invention a method for creating a stable antibody ionic liquid comprises: a) providing aqueous antibodies, wherein the antibodies are one of anti-A antibodies, anti-B antibodies, and anti-Rh antibodies; b) cationizing the aqueous antibodies by the addition of stoichiometric amounts of an excess of a positively-charged crosslinker in the presence of a coupling reagent; and c) titrating the cationized antibodies with a counter anionic polymer, forming an antibody cation/anion pair solution, until the antibody cation/anion pair solution becomes negative by zeta potential measurement to create at least one antibody cation/anion pair in aqueous solution. A negative zeta potential of the titrated cationized antibodies ensures that there is a minor excess of anion but that the positive charges are equally balanced. A stoichiometric addition means that there is at least enough crosslinker and coupling agent present to cationize the protein/antibody to the desired degree. A slight excess of crosslinker and coupling agent is acceptable.

According to a first variation of the embodiment, the method further comprises d) lyophilizing the antibody cation/anion pair solution to remove all of the water, forming a lyophilized solid. Removal of all water means removal of at least 95% or at least 99% of the water.

According to another variation, the method further comprises e) heating the lyophilized solid until an antibody ionic liquid is generated. The lyophilized solid may be heated up to about 50° C. to generate the antibody ionic liquid. Heating of the lyophilized solid may be done on a hotplate, in a temperature controlled water bath, or an oven at about 27-50° C., for example. This provides the advantage of producing stable, heat-resistant, biologically active protein ionic liquids that do not require refrigeration. In one embodiment of the present invention, the protein ionic liquid is a viscous, clear liquid. Antibodies may include but are not limited to IgG, IgY, IgM, and other proteins or negatively-charged molecules may also be rendered stable according to the teachings herein.

According to a further variation, the cationized antibodies may be purified from excess coupling reagents by dialysis in water. Dialysis may be performed repeatedly until the desired purity is achieved. This provides the advantage of obtaining a pure sample composed of only antibodies modified with positive charges.

According to another variation, the aqueous antibodies are cationized by the addition of stoichiometric amounts of N,N-dimethyl-1,3-propanediamine in the presence of 1-ethyl-3-(3-dimethylaminopropyl) carbodiimide (EDC) coupling reagent; the addition of succinimidyl iodoacetate (SIA) in the presence of 2-(dimethylamino) ethanethiol; and/or the addition of N-(p-maleimidophenyl) isocyanate (PMPI) in the presence of 2-(dimethylamino) ethanethiol. These pairs of crosslinkers and coupling reagents are demonstrated to cationize each of the antibodies identified below.

According to a further variation, the crosslinker is one or more selected from the group consisting of N,N-dimethyl-1,3-propanediamine, 2-(dimethylamino) ethanethiol, 4-(Dimethylamino)cinnamaldehyde, 3-(Dimethylamino)propionic acid hydrochloride, 5-(Dimethylamino)amylamine, or 4-(Dimethylamino)-2-butenoic acid hydrochloride.

According to another variation, the coupling reagent is one or more selected from the group consisting of 1-ethyl-3-(3-dimethylaminopropyl) carbodiimide (EDC), succinimidyl iodoacetate (SIA), N-(p-maleimidophenyl) isocyanate (PMPI), N-α-maleimidoacet-oxysuccinimide ester (AMAS), N-β-maleimidopropyl-oxysuccinimide (BMPS), succinimidy 3-(bromoacetamido) propionate (SBAP), N-5-azido-2-nitrobenzoylsuccinimide (ANB-NOS), sulfosuccinimidyl-4,4'-azipentanoate (sulfo-SDA), and N-β-maleimidopropionic acid hydrazide (BMPH).

According to a further variation, the aqueous antibodies are cationized by the addition of 3-(Dimethylamino)propionic acid hydrochloride, 5-(Dimethylamino)amylamine, or 4-(Dimethylamino)-2-butenoic acid hydrochloride in the presence of 1-ethyl-3-(3-dimethylaminopropyl) carbodiimide (EDC).

According to another variation, the aqueous antibodies are cationized by the addition of N,N-dimethyl-1,3-propanediamine in the presence of 1-ethyl-3-(3-dimethylaminopropyl) carbodiimide (EDC), N—S-azido-2-nitrobenzoylsuccinimide (ANB-NOS), or sulfosuccinimidyl-4,4'-azipentanoate (sulfo-SDA).

According to a further variation, the aqueous antibodies are cationized by the addition of succinimidyl iodoacetate (SIA), N-(p-maleimidophenyl) isocyanate (PMPI), N-α-maleimidoacet-oxysuccinimide ester (AMAS), N-β-maleimidopropyl-oxysuccinimide (BMPS), succinimidy 3-(bromoacetamido) propionate (SBAP), or N-β-maleimidopropionic acid hydrazide (BMPH) in the presence of 2-(dimethylamino) ethanethiol. These crosslinkers and coupling reagents are demonstrated to cationize each of the antibodies identified below.

According to another variation, the at least one antibody cation/anion pair, after titration, may be dialyzed to remove excess anionic polymer with at least one membrane having a molecular weight cutoff of between about 6000-15,000 g/mol, e.g. about 7000 g/mol. This membrane may separate a plurality of contaminants and excess reagents from the modified proteins that are below a molecular weight, e.g. 7000 g/mol. A molecular weight of at least about 7000 g/mol typically ensures that all coupling reagents, positively-charged cross-linker, and buffer salts are separated from cationized proteins. About 7000 g/mol may be the lower limits for this dialysis, however, the membrane could be as large as 15,000 g/mol, but at the risk of losing proteins through the larger membrane.

According to a further variation, the cationization of the aqueous antibodies may be confirmed by measuring a positive zeta potential value, e.g. between about 0 and +5 mV. This provides the advantage of determining/quantifying the number of positive charges added to the protein.

According to another variation, the aqueous antibodies are cationized by the addition of stoichiometric amounts of N,N-dimethyl-1,3-propanediamine in the presence of 1-ethyl-3-(3-dimethylaminopropyl) carbodiimide (EDC) coupling reagent; the addition of succinimidyl iodoacetate (SIA) in the presence of 2-(dimethylamino) ethanethiol; and/or the addition of N-(p-maleimidophenyl) isocyanate (PMPI) in the presence of 2-(dimethylamino) ethanethiol.

According to a further variation, the counter anionic polymer is a biologically-compatible anionic polymer comprising at least one of Poly(ethylene glycol) 4-nonylphenyl 3-sulfopropyl ether ($C_9H_{19}C_6H_4$—$(OCH_2CH_2)_{20}$ $O(CH_2)_3SO_3$), DL-lactate, linolenate, phospholipids, fatty acids, the conjugate base form of all amino acids (i.e. deprotonated and negatively charged), any biologically-derived singly-charged anions with low melting points (e.g. between about 5-30° C.), and small DL-peptide pairs. This provides the advantage of balancing the positive charges on the antibody with negative charges of the anion to form the ionic salt form of the antibody.

According to another variation, the aqueous antibodies are cationized by the addition of 3-(Dimethylamino)propionic acid hydrochloride, 5-(Dimethylamino)amylamine, or 4-(Dimethylamino)-2-butenoic acid hydrochloride in the presence of 1-ethyl-3-(3-dimethylaminopropyl) carbodiimide (EDC).

According to a further variation, the aqueous antibodies are cationized by the addition of N,N-dimethyl-1,3-propanediamine in the presence of 1-ethyl-3-(3-dimethylaminopropyl) carbodiimide (EDC), N-5-azido-2-nitrobenzoylsuccinimide (ANB-NOS), or sulfosuccinimidyl-4,4'-azipentanoate (sulfo-SDA).

According to another variation, the aqueous antibodies are cationized by the addition of succinimidyl iodoacetate (SIA), N-(p-maleimidophenyl) isocyanate (PMPI), N-α-maleimidoacet-oxysuccinimide ester (AMAS), N-β-maleimidopropyl-oxysuccinimide (BMPS), succinimidy 3-(bromoacetamido) propionate (SBAP), or N-β-maleimidopropionic acid hydrazide (BMPH) in the presence of 2-(dimethylamino) ethanethiol. The crosslinker becomes integrated into the antibody, but the EDC coupling reagent does not. EDC becomes a byproduct of reaction. However, the other coupling reagents do become part of the antibody and are partially integrated with cross-linker. i.e. SBAP, BMPH, sulfo-SDA, PMPI, AMAS, and BMPS.

According to a second embodiment, a stable antibody ionic liquid comprises an anti-hemoglobin cation/anion pair at least one of anti-A antibodies, anti-B antibodies, and anti-Rh antibodies.

According to a first variation of the second embodiment, the antibody cation/anion pair further comprises an anionic polymer selected from the group consisting of poly(ethylene glycol) 4-nonylphenyl 3-sulfopropyl ether ($C_9H_{19}C_6H_4$—$(OCH_2CH_2)_{20}O(CH_2)_3SO_3$), DL-lactate, linolenate, phospholipids, fatty acids, the conjugate base form of all amino acids, biologically-derived singly-charged anions, and small DL-peptide pairs.

According to another variation, the method for creating a stable protein/antibody ionic liquid further comprises heating the protein/antibody ionic liquid at about 100° C. for about 2 hours; and testing the protein/antibody ionic liquid for antibody recognition of a corresponding antigen, when the protein is an antibody. In one embodiment, the testing may be done using a dot blot assay on a nitrocellulose membrane. In a further embodiment, the heating may be between about 75° C. and about 150° C. and/or may be between 1 and 3 hours. This provides the advantage of evaluating the temperature stability of the protein/antibody ionic liquid at extreme temperatures by directly measuring binding activity of the antibody for an antigen.

According to a further variation, the protein is one or more of anti-hemoglobin antibodies, polyclonal anti-horse spleen ferritin antibodies, monoclonal Anti-Flag antibodies, monoclonal Anti-HRP2 to *Plasmodium falciparum*, polyclonal Anti-neuropeptide Y, polyclonal Anti-human troponin, and all antibody isotypes, e.g. IgY, IgG, IgM, IgE, etc. Each of these proteins may be stabilized according to the same method described above for the disclosed antibodies.

In addition, a dye, such as an IR active dye, may be combined with blood-typing antibody solutions via conjugation of an amine reactive dye, e.g., Anti-A (an IgM antibody) ionic liquid, such that blood typing may be accomplished without visible light using night vision goggles to determine blood type via the hemagluttination of red blood cells, a tremendous boon to soldiers and field medics in hazardous regions. Other variations may be useful for lateral flow assays, enzyme-linked immunosorbent assays (ELISA), anti-venom/anti-toxin therapeutics, immunotherapy, vaccines, anti-virals, detection of chemical, biological, nuclear, environmental and radioactive agents, and may be applied to other biologically-important proteins whether negatively or positively charged, e.g., insulin.

According to a second embodiment of the invention, a method comprises the steps of: a) providing aqueous antibodies; b) cationizing the aqueous antibodies by adding stoichiometric amounts of a crosslinker (e.g. one or more of N,N-dimethyl-1,3-propanediamine (DMPDA), 4-(Dimethylamino)cinnamaldehyde or 3-(Dimethylamino)propionic acid hydrochloride or 5-(Dimethylamino)amylamine and 4-(Dimethylamino)-2-butenoic acid hydrochloride) in the presence of a coupling reagent (e.g. one or more of 1-ethyl-3-(3-dimethylaminopropyl) carbodiimide (EDC), succinimidyl iodoacetate (SIA), 2-(dimethylamino) ethanethiol, and N-(p-maleimidophenyl) isocyanate (PMPI)); and c) titrating the cationized antibodies with a counter anionic polymer (e.g. one or more of poly(ethylene glycol) 4-nonylphenyl 3-sulfopropyl ether $(C_9H_{19}C_6H_4—(OCH_2CH_2)_{20}O(CH_2)_3SO_3)$, DL-lactate, linolenate, phospholipids (e.g. phosphatidylserine), fatty acids (e.g. stearic acid, palmitic acid, oleic acid, linolenic acid), the conjugate base form of all amino acids (i.e. the ionic form where the carboxylate group of the amino acid is deprotonated), biologically-derived singly-charged anions (e.g. small peptides such as Ac—NH$_2$-AAAAAAA-CO$_2$), and small DL-peptide pairs) to create at least one antibody cation/anion pair in aqueous solution until the antibody cation/anion pair solution becomes negative by zeta potential measurement.

According to a further variation of the second embodiment, the method may further comprise: dialyzing the at least one antibody cation/anion pair to remove excess anionic polymer using a dialysis membrane having a molecular weight cutoff between 6000 and 15,000 g/mol. The dialysis membrane may be selected to remove to selectively separate the desired components. Any sub-range between 6000 and 15,000 g/mol may be selected, e.g. 6000-12,000, 6000-10,000, 6000-8000, etc., or a single value selected to separate the desired components, e.g. 7000 g/mol. The dialysis step is optional but may be considered important if high purity, i.e. for medical or therapeutic human or animal use, is desired. A dialysis (or purification) step may be performed after cationization and/or after titration. Where dialysis is performed after cationization, it may be helpful to distinguish the dialysis step as purifying the cationized proteins from excess coupling reagents by dialysis in water. This provides the advantage of obtaining a pure antibody sample composed of only antibodies modified with positive charges. The purification step may be performed after the cationizing step, if desired, depending upon the desired results. For example, it may be highly desired to purify antibodies which are intended for medical use in order to improved efficacy and to decrease the likelihood of adverse reactions. The particular molecular weight target may be selected according to the desired results and the particular antibodies being processed.

According to another variation of the second embodiment, the method may further comprise: lyophilizing the at least one antibody cation/anion pair to remove most of the water, forming a lyophilized solid. The lyophilized antibodies are shelf-stable and do not require refrigeration. Removing "most of the water", "all of the water", or "water-free" requires removal of at least 95% of the water, and in some embodiments more than 99% of the water.

According to a further variation of the second embodiment, the antibodies are one of anti-hemoglobin antibodies, anti-horse spleen ferritin IgG antibodies, or blood-typing IgM Anti-A antibodies, single-chain antibodies from camelids, monoclonal Anti-Flag antibodies, monoclonal Anti-HRP2 to *Plasmodium falciparum*, polyclonal Anti-neuropeptide Y, and polyclonal Anti-human troponin. It has been discovered that antibodies of different types, including those specifically named above, are able to be stabilized and made into ionic liquids by the disclosed method.

According to another variation of the second embodiment, the method further comprises: confirming the cationizing of the aqueous antibodies by measuring a positive zeta potential value. When cationizing the aqueous antibodies, a minimum zeta potential value between 0 and about +5 mV is desired for cationization. This step is optional, but may be useful simply to confirm cationization has properly taken place.

According to a further variation of the second embodiment, when titrating the cationized antibodies, the negative zeta potential desired is below 0 mV to about −1 mV by zeta potential. A negative zeta potential of the titrated cationized antibodies ensures that there is a minor excess of anion but that the positive charges are equally balanced. In one embodiment of the present invention, the protein ionic liquid is a viscous, clear liquid. Antibodies may include but are not limited to IgG, IgY, IgM; other proteins or negatively-charged molecules may also be rendered stable according to the teachings herein.

According to another variation of the second embodiment, the method may further comprise heating the lyophilized solid at about 27-50° C. until an antibody ionic liquid is generated. This may take approximately 20-30 minutes of heating.

According to a further variation of the second embodiment, the method may further comprise heating the water-free ultra-stable protein ionic liquid at about 100° C. for about 2 hours, and testing the antibody ionic liquid for antibody recognition of a corresponding antigen. This optional step relates to the determination of the thermal limits appropriate for storage, i.e. long-term unrefrigerated storage, of the stabilized antibodies. Although 100° C. is provided herein, different thermal limits, e.g. 50° C., 150° C., 200° C., or temperatures anywhere between may be chosen, depending on the required efficacy of the stabilized antibodies and the relative fragility of the antibodies. Testing of the antibody ionic liquid for antibody recognition of a corresponding antigen may be made using a dot blot assay on a nitrocellulose membrane.

According to a further variation of the second embodiment, the crosslinker may be one or more selected from the group of N,N-dimethyl-1,3-propanediamine, 2-(dimethylamino) ethanethiol, 4-(Dimethylamino)cinnamaldehyde, 3-(Dimethylamino)propionic acid hydrochloride or 5-(Dimethylamino)amylamine, and 4-(Dimethylamino)-2-butenoic acid hydrochloride. It was found that the listed crosslinkers are each effective and may be successfully used interchangeably with each of the disclosed antibodies.

According to a another variation of the second embodiment, the coupling reagent may be one or more selected from the group of 1-ethyl-3-(3-dimethylaminopropyl) carbodiimide (EDC), succinimidyl iodoacetate (SIA), N-(p-maleimidophenyl) isocyanate (PMPI), N-α-maleimidoacet-oxysuccinimide ester (AMAS), N-β-maleimidopropyl-oxysuccinimide (BMPS), succinimidy 3-(bromoacetamido) propionate (SBAP), N-5-azido-2-nitrobenzoylsuccinimide (ANB-NOS), sulfosuccinimidyl-4,4'-azipentanoate (sulfo-SDA), and N-β-maleimidopropionic acid hydrazide (BMPH).

EDC, ANB-NOS, and sulfo-SDA cross-linkers each work with N,N-dimethyl-1,3-propanediamine, 5-(dimethylamino) amylamine, 3-(dimethylamino)propionic acid, and 5-9dimethylamino)-2-butenoic acid. SIA, PMPI, AMAS, BPMS, SBAP, and BMPH each work interchangeably with 2-(dimethylamino) ethanethiol. It was found that the listed coupling reagents are each effective and may be successfully used interchangeably with each of the disclosed antibodies. Various combinations of the crosslinkers and coupling reagents may be made, including cationizing aqueous proteins by addition of an excess of or a stoichiometric amount of N,N-dimethyl-1,3-propanediamine crosslinker in the presence of 1-ethyl-3-(3-dimethylaminopropyl) carbodiimide (EDC) coupling reagent; cationizing aqueous proteins by addition of an excess of or a stoichiometric amount of 2-(dimethylamino) ethanethiol crosslinker in the presence of succinimidyl iodoacetate (SIA) coupling agent; or cationizing aqueous proteins by addition of an excess of or a stoichiometric amount of 2-(dimethylamino) ethanethiol crosslinker in the presence of N-(p-maleimidophenyl) isocyanate (PMPI) coupling agent, which are provided merely as examples, and not intended as limiting.

According to a further variation of the second embodiment, beyond the example of poly(ethylene glycol) 4-nonylphenyl 3-sulfopropyl ether $(C_9H_{19}C_6H_4—(OCH_2CH_2)_{20}O(CH_2)_3SO_3)$ described above, several other biologically-compatible counter anionic polymers are acceptable for use, and are interchangeable and combinable, including DL-lactate, linolenate, phospholipids, fatty acids, the conjugate base form of all amino acids, biologically-derived singly-charged anions, and small DL-peptide pairs.

According to another variation of the first embodiment, the method for creating a water-free ultra-stable ionic liquid may further comprise heating the lyophilized solid at about 27-50° C. until an antibody ionic liquid is generated. Heating of the lyophilized solid may be done on a hotplate, in a temperature controlled water bath, or an oven at about 27-50° C., for example. The optional heating step demonstrates that a stable, heat-resistant antibody ionic liquid is formed.

According to a further embodiment of the invention, a water-free ultra-stable ionic liquid comprises a cation/anion pair comprising one of an anti-hemoglobin antibodies, polyclonal anti-horse spleen ferritin antibodies, blood-typing anti-A antibodies, single-chain antibodies from camelids, monoclonal Anti-Flag antibodies, monoclonal Anti-HRP2 to *Plasmodium falciparum*, polyclonal Anti-neuropeptide Y, and polyclonal Anti-human troponin. Such antibody ionic liquids may be made according to the disclosed method.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

This invention exploits the physical properties of ionic liquids and the biological recognition of antigen-specific antibodies to create a stable and heat-resistant antibody protein ionic liquid that exhibits refrigeration-free storage and handling, which makes it suitable for use or storage at typical room temperatures. However, such a process has numerous obstacles to overcome because antibodies and many other proteins are negatively charged. This makes such proteins and antibodies difficult to ionically combine with anions. In order to create an ionic liquid with antibodies, the antibodies' charge must be made more positive. Antibodies have a great number of negative sites (e.g. carboxyl groups, —COOH; amine groups —NH$_2$; hydroxyl groups, —OH) to address, but in order to maintain the activity of the antibody the cationization process should not be too aggressive. In short, too few positive charges yields an antibody that does not function correctly as a salt. Too many positive charges yields an antibody with diminished biological activity, i.e. once the antibody's non-acid (general) amino acids are coupled the antibody loses its specificity and its usefulness.

Figure 1:
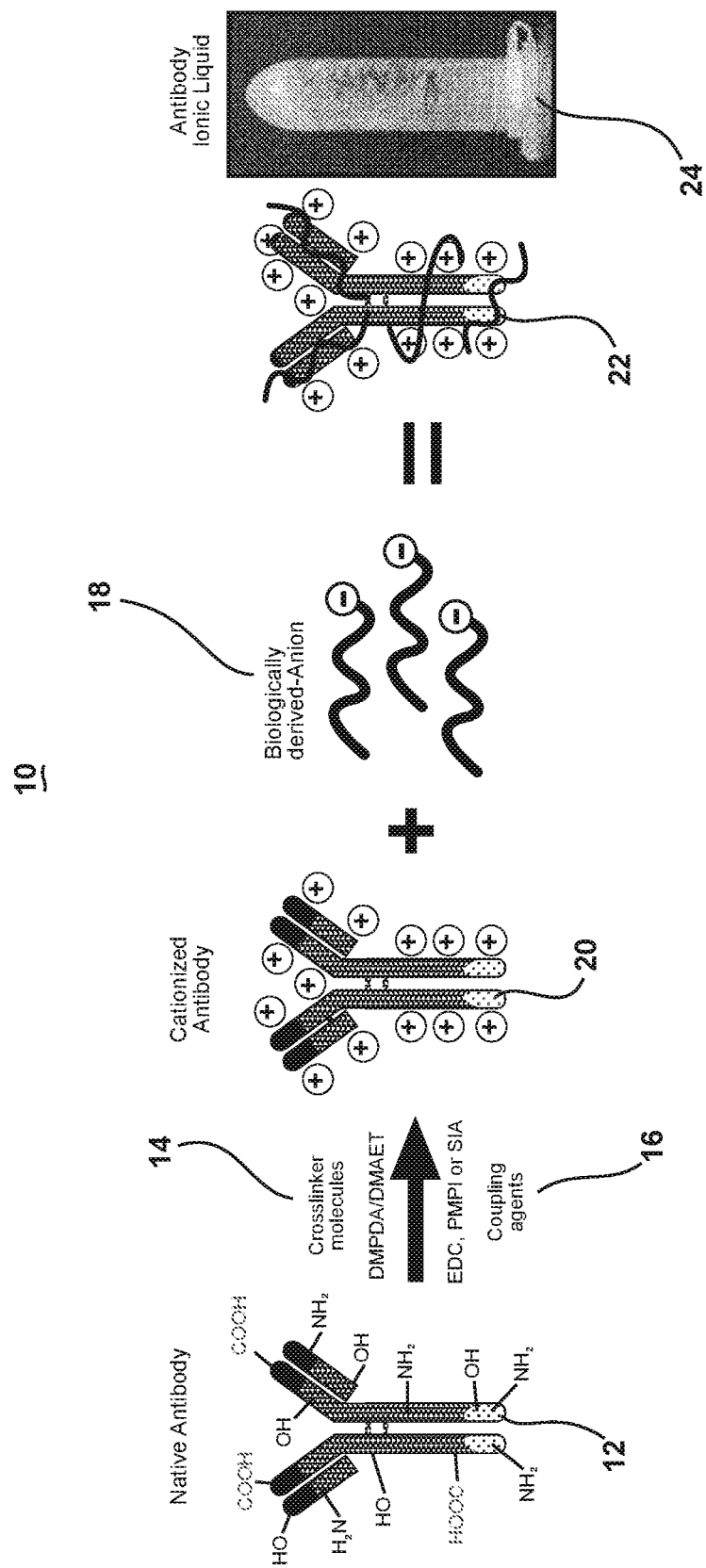
FIG. 1 depicts a general approach to modify any protein or antibody into a stable protein or antibody, according to an embodiment of the present invention.

FIG. 1 depicts a general approach 10 to modify any antibody, e.g. a native antibody. In one embodiment, four solutions may be required to produce an antibody ionic liquid: a solution of antibodies 12, a solution of cationic crosslinker molecules 14, a solution of coupling agents 16, and a corresponding anion 18. The anion 18 may be biologically-derived or abiotic. The examples presented herein utilize biologically-derived anions, but abiotic anions may be used in the same manner. After the antibodies 12 are cationized (cationized antibodies 20 with cationic crosslinker molecules depicted as "+"), biologically-derived (or biologically-compatible) anions 18 are combined with the cationized antibodies 20 to form an antibody/anion salt 22. Removal of all or most of the water, i.e. at least 95% or at least 99%, results in an ultra-stable antibody ionic liquid 24, which is depicted in a sample tube. The antibody ionic liquid 24 may require no refrigeration, may be stable (i.e. retains efficacy and functionality) at room temperature, and may be stable up to about 200° C.

Figure 2:
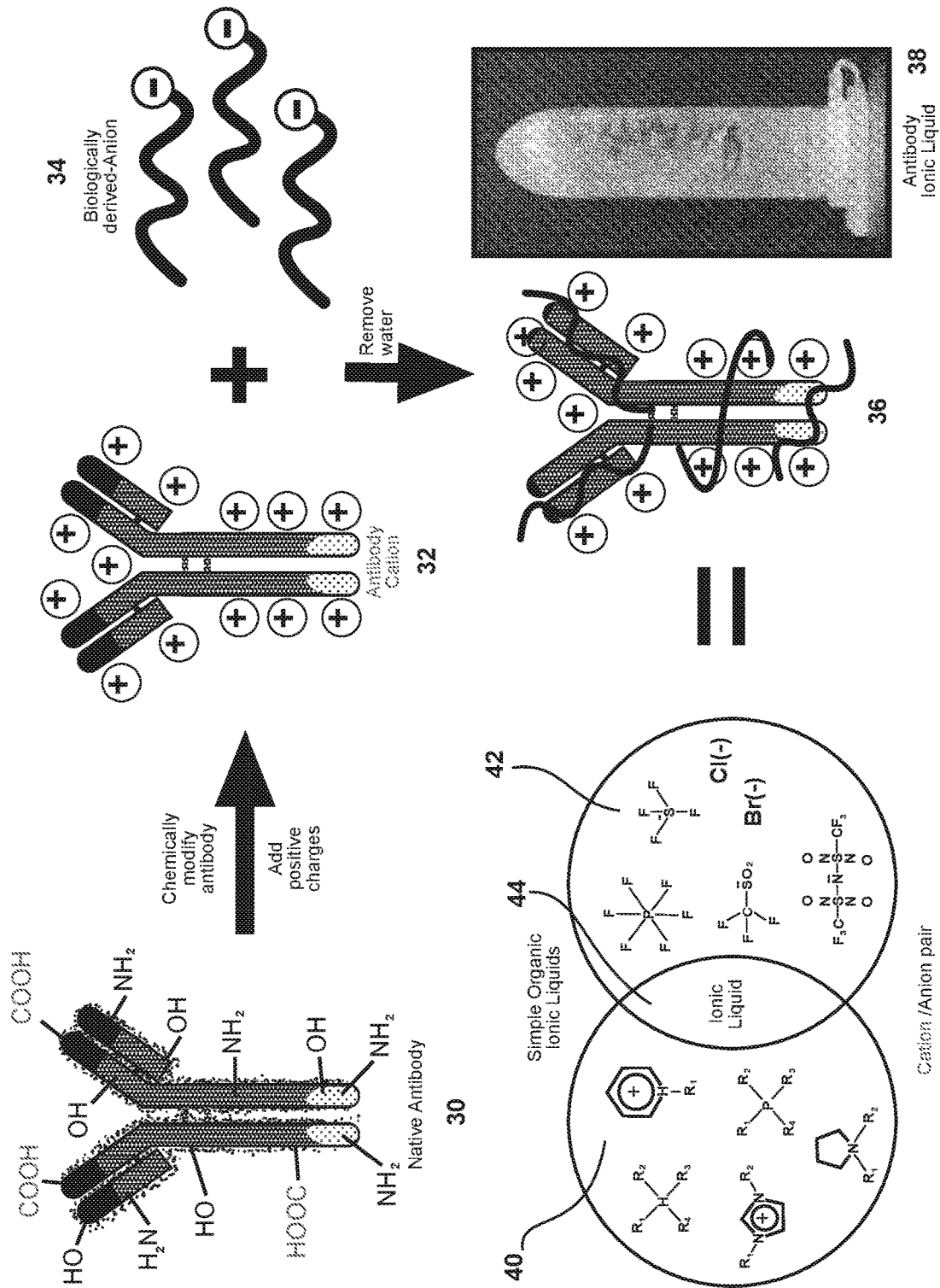
FIG. 2 depicts a more-detailed approach to modify any protein or antibody into a stable protein or antibody, according to an embodiment of the present invention.

FIG. 2 depicts another embodiment of the invention to modify any antibody. Some of the numerous acidic sites, i.e., —COOH (carboxyl), basic sites —NH2 (amine), and neutral sites —OH (hydroxyl) are depicted on a native (unmodified) antibody 30. At least some of the carboxyl, amine, and hydroxyl groups may be modified in order to achieve a cationic antibody 32, i.e. the carboxyl, amine, and hydroxyl groups (depicted on native antibody 30) of the native antibody 30 are negative sites which tend to make the native antibody 30 generally anionic. This may be done selectively. Various cations may be used to selectively modify the carboxyl, amine, and hydroxyl groups. For example, EDC (1-ethyl-3-(3-dimethylaminopropyl) carbodiimide) may be used to modify the carboxyl groups, SIA (succinimidyl iodoacetate) may be used to modify the amine groups, and PMPI (N-(p-maleimidophenyl) isocyanate) may be used to modify the hydroxyl groups (not shown) to form an antibody cation 32. Cations in FIG. 32 are represented by "+". If only a fraction of each carboxyl, amine, and hydroxyl group is desired to be modified, in order to maintain the functionality of the antibody salt, the stoichiometry may be adjusted to limit the reagents (e.g., EDC, SIA, PMPI) and thereby limit the number of groups, i.e. the carboxyl, amine, and hydroxyl groups, which are modified. After the antibody is cationized 32, the cationized antibody 32 may be combined with an anion 34 in order to form an antibody ionic liquid 36 after removal of most or all of the water. The antibody ionic liquid 36 is depicted in a sample tube 38.

Figure 3:
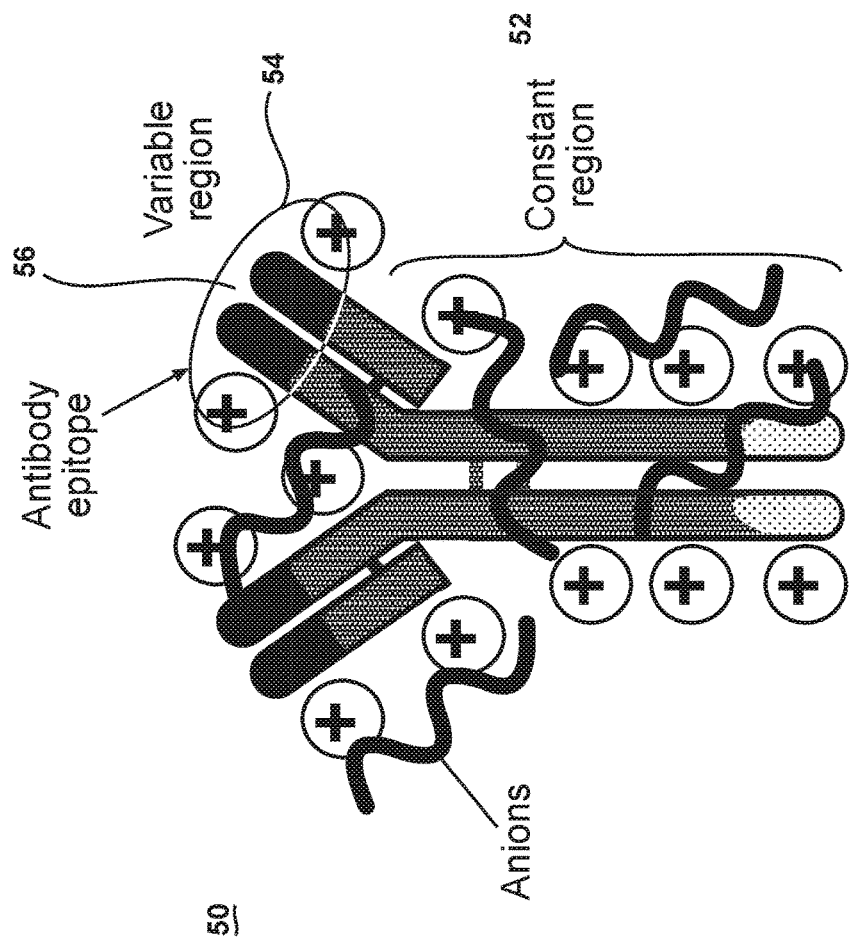
FIG. 3 depicts a typical protein or antibody that has been cationized, according to the present invention.

FIG. 3 depicts a typical antibody 50 (e.g. anti-hemoglobin antibodies, anti-horse spleen ferritin IgG antibodies, or blood-typing IgM Anti-A antibodies, single-chain antibodies from camelids, monoclonal Anti-Flag antibodies, monoclonal Anti-HRP2 to *Plasmodium falciparum*, polyclonal Anti-neuropeptide Y, and polyclonal Anti-human troponin) that has been cationized. A typical antibody 50 has a constant region 52 and a variable region 54. The constant region 52 (corresponding to about the lower two-thirds of the depicted antibody 50) is generally the same for antibodies. The variable region 54, depicted as the upper ends of the Y branches, includes an antibody epitope 56 which will be distinct for each different type of antibody, depending on its affinity for a specific antigen. This gives the antigen its functionality. In one embodiment, only the constant region 52 is modified so as to retain the functionality of the antigen 50. Even with fewer than only about 5-15% of the amino acids in the constant region 52 modified taking into account the total number of amino acids in the constant region, or about 60-90% of the negative sites in the constant region, the resulting antibody ionic liquid will exhibit binding affinity and functionality with appropriate antigens.

Figure 4:
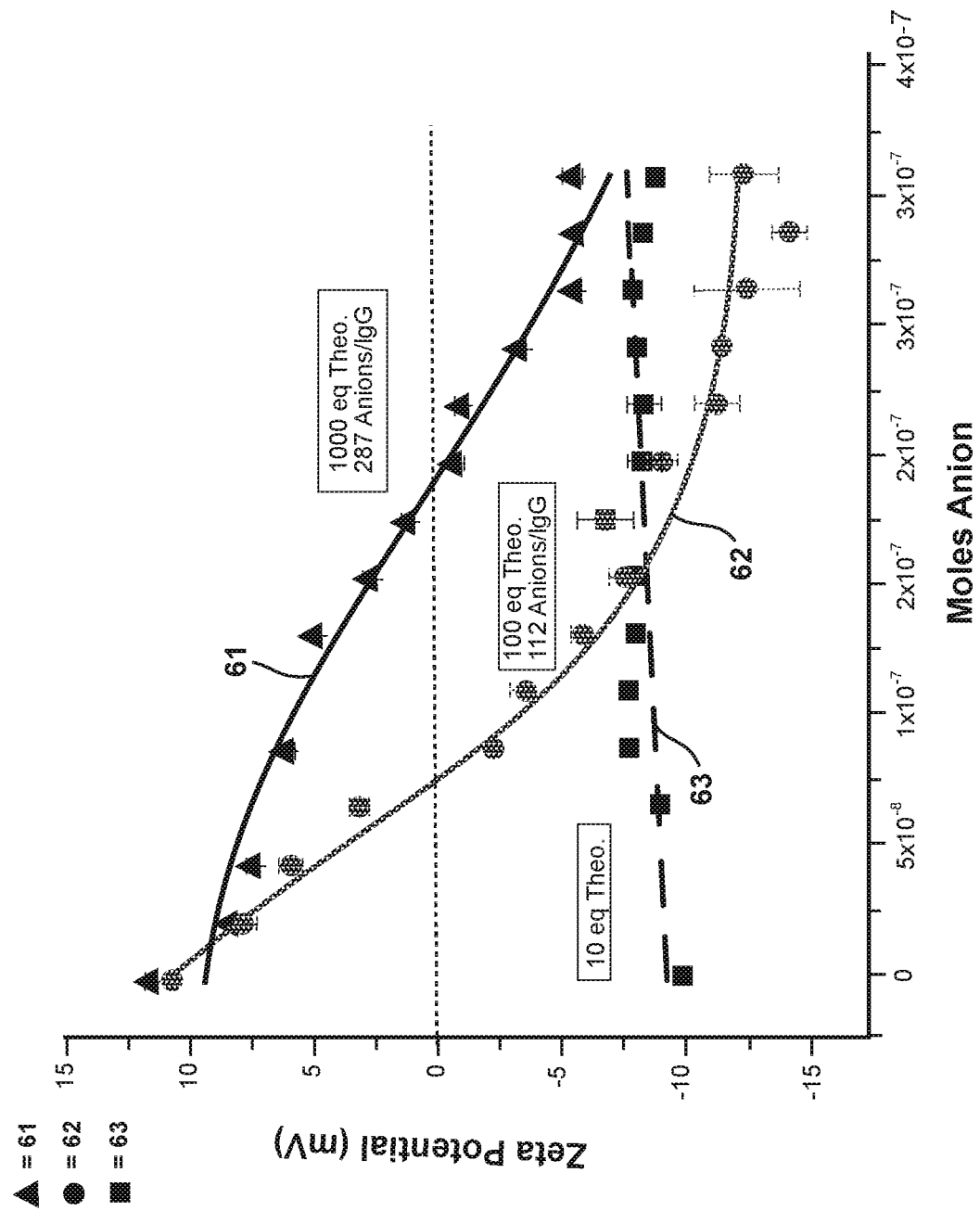
FIG. 4 depicts the cationization of a protein or antibody solution in the presence of a coupling agent, according to an embodiment of the present invention.

FIG. 4 depicts the cationization of an antibody solution with a crosslinker (e.g. N,N-dimethyl-1,3-propanediamine, 2-(dimethylamino) ethanethiol, 4-(Dimethylamino)cinnamaldehyde or 3-(Dimethylamino)propionic acid hydrochloride or 5-(Dimethylamino)amylamine and 4-(Dimethylamino)-2-butenoic acid hydrochloride) in the presence of a coupling agent (e.g. 1-ethyl-3-(3-dimethylaminopropyl) carbodiimide (EDC), succinimidyl iodoacetate (SIA), N-(p-maleimidophenyl) isocyanate (PMPI), N-α-maleimidoacetoxysuccinimide ester (AMAS), N-β-maleimidopropyloxysuccinimide (BMPS), succinimidy 3-(bromoacetamido) propionate (SBAP), N-5-azido-2-nitrobenzoylsuccinimide (ANB-NOS), sulfosuccinimidyl-4,4'-azipentanoate (sulfo-SDA), and N-β-maleimidopropionic acid hydrazide (BMPH)) in the presence of a coupling agent. In one embodiment, cationization gives the antibody a positive charge without neutralizing its functionality. Too few positive charges means the antibody will not form an ionic liquid with an anion. Too many positive charges may result in the antibody losing its functionality. This balance is determined empirically. We start with a highly cationized antibody and determine any changes in binding activity. If binding activity is affected, we add fewer positive charges. FIG. 4 graphically illustrates how the concentrations of the coupling agents may affect the overall charge of the antibodies, and accordingly, about how many anions will be bound with the cationic antibodies. There are about 144 acidic amino acids on a typical antibody, and about 1600 total (acidic and non-acidic) amino acids. The non-acidic amino acids control the functionality of the antibodies. If too many (more than about 30% of the total amino acids) non-acid amino acids are coupled the antibody loses its specificity and affinity, i.e. it no longer functions as an antibody. The chart of FIG. 4 illustrates that there is a practical limit as to how many anions may be bound by a cationic antibody. The dashed line (line 63 with square data points) illustrates a cationic antibody solution that has been cationized at about 10 equivalents (theoretic—about 10 positive charges per IgG antibody) based on the strength of the coupling agents. Line 63 starts with a negative zeta potential, which indicates that the cationization was insufficient to give the antibodies a positive charge overall. Thus this low level of cationization is insufficient for use in making an antibody ionic liquid.

Line 62 (solid line with circle data points) illustrates a cationic antibody solution that has been cationized at about 100 equivalents (theoretic) based on the strength of the coupling agents. Line 62 starts with a positive zeta potential, which indicates that the cationization was sufficient to give the antibodies a positive charge overall. Thus this level of cationization is sufficient for use in making an antibody ionic liquid. Likewise, line 61 (solid line with triangle data points) illustrates a cationic antibody solution that has been cationized at about 1000 equivalents (theoretic) based on the strength of the coupling agents. Line 61 starts with a positive zeta potential, which indicates that the cationization was sufficient to give the antibodies a positive charge overall. Thus this level of cationization is also sufficient for use in making an antibody ionic liquid. However, the extra strength of the coupling agents did not affect the formation of the ionic liquid to the degree expected from the concentration of the coupling agents.

Figures 5A, 5B:
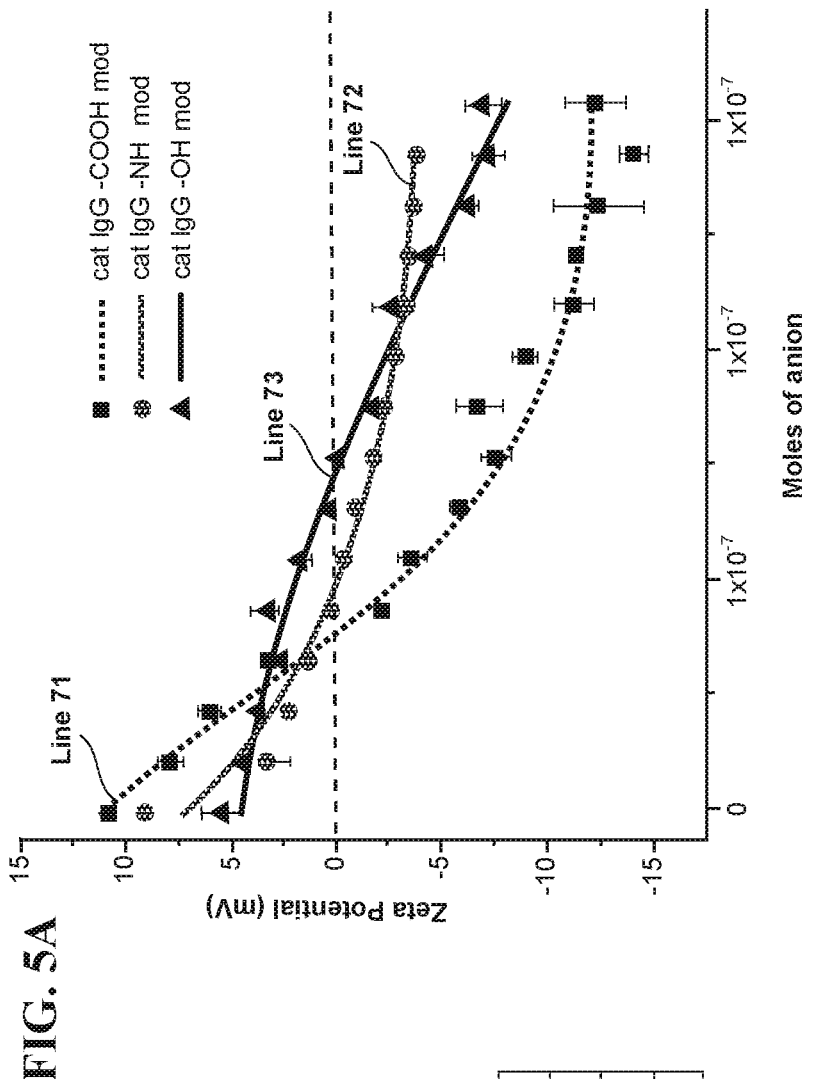
FIGS. 5A-5B depict the selective cationization of IgG in the presence of coupling agents, according to an embodiment of the present invention.

FIG. 5A depicts another embodiment of the invention with the selective cationization of immunoglobulin (IgG) in the presence of coupling agents. There are different numbers of the carboxyl, amine, and hydroxyl groups in a typical antibody. These may be selectively coupled through the use of particular coupling agents, including, for example, SIA, PMPI, AMAS (N-α-maleimidoacet-oxysuccinimide ester), BMPS (N-(3-maleimidopropyl-oxysuccinimide), SBAP (succinimidy 3-(bromoacetamido) propionate), a photoactive coupling agent (e.g. ANB-NOS (N-5-azido-2-nitrobenzoylsuccinimide) or sulfo-SDA (sulfosuccinimidyl-4,4'-azipentanoate)), or BMPH (N-β-maleimidopropionic acid hydrazide), and combinations thereof. AMAS, BMPS, or SBAP may be used as a substitute for SIA. For example, SIA may be used to cationize the amine (—NH2) sites, and PMPI may be used to cationize the hydroxyl (—OH) groups. Selective cationization of these groups in the antibodies may be accomplished with selected coupling agents, and/or the use of selected coupling agents as limited reagents, in order to achieve a desired cationic state or positive zeta potential. Line 71 (line with square data points) corresponds to the cationization of carboxyl (—COOH) groups, line 72 (line with circular data points) corresponds to the cationization of amine (—NH) groups), and line 73 (line with triangular data points) corresponds to the cationization of hydroxyl (—OH) groups). In one embodiment of the present invention, each of these groups may be selectively and/or partially cationized to achieve the desire cationic state or zeta potential in order to function properly as an ionic liquid. FIG. 5B illustrates a comparison between the theoretical total number of amino acid groups (—COOH or NH2 or —OH) which may be modified with a positive charge and the actual number that were modified in a particular experiment. Out of a total of 144 —COOH groups (corresponding to line 1 of the graph presented on FIG. 5A), 115 of those were modified, leaving 29 —COOH groups unmodified.

Next, the cationized antibodies are titrated with a counter anionic polymer (e.g. one or more of poly(ethylene glycol) 4-nonylphenyl 3-sulfopropyl ether ($C_9H_{19}C_6H_4$—($OCH_2CH_2$)$_{20}$O($CH_2$)$_3SO_3$), DL-lactate, linolenate, phospholipids, fatty acids, the conjugate base form of all amino acids, biologically-derived singly-charged anions, and small DL-peptide pairs) to create at least one antibody cation/anion pair in aqueous solution until the antibody cation/anion pair solution becomes negative by zeta potential measurement. The same methodology is applicable to each of the disclosed antibodies, generally applicable to all antibodies, and yields antibody ionic liquids which are stable and maintain efficacy up to 200° C., as illustrated in FIG. 7.

Figure 6:
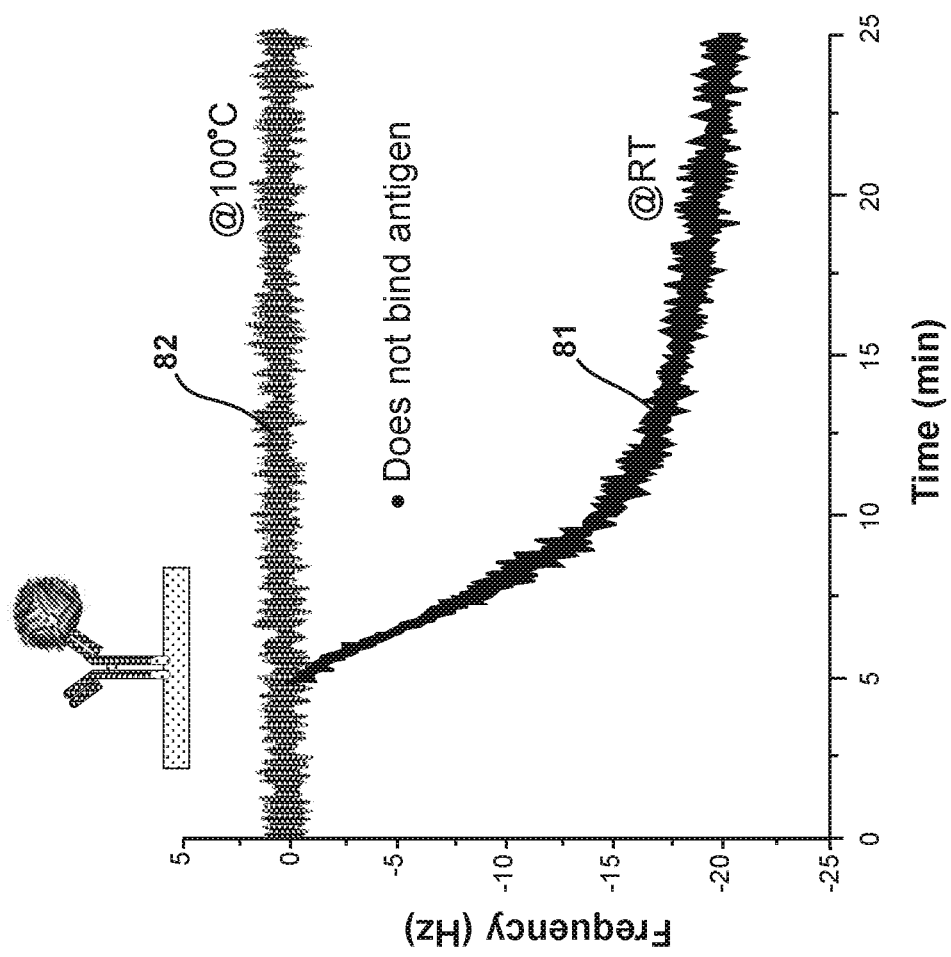
FIG. 6 depicts the antigen binding of an aqueous antibody at room temperature and at 100° C., according to an embodiment of the present invention.

FIG. 6 depicts the antigen binding of an aqueous antibody at room temperature (i.e. about 21-25° C.) 81 and at 100° C. 82 using a quartz crystal microbalance (QCM) to measure mass of antigen adsorbed to an antibody immobilized quartz sensor. FIG. 6 illustrates that an aqueous antibody solution cannot handle elevated temperatures, as is depicted by the change in frequency response as temperature increases. As the temperature increases to 100° C., the antibody solution exhibits decreasing binding activity until no binding activity is seen. That is, no binding is observed when a constant frequency value of 0 Hz+/−0.5 Hz over time is measured.

Figure 7:
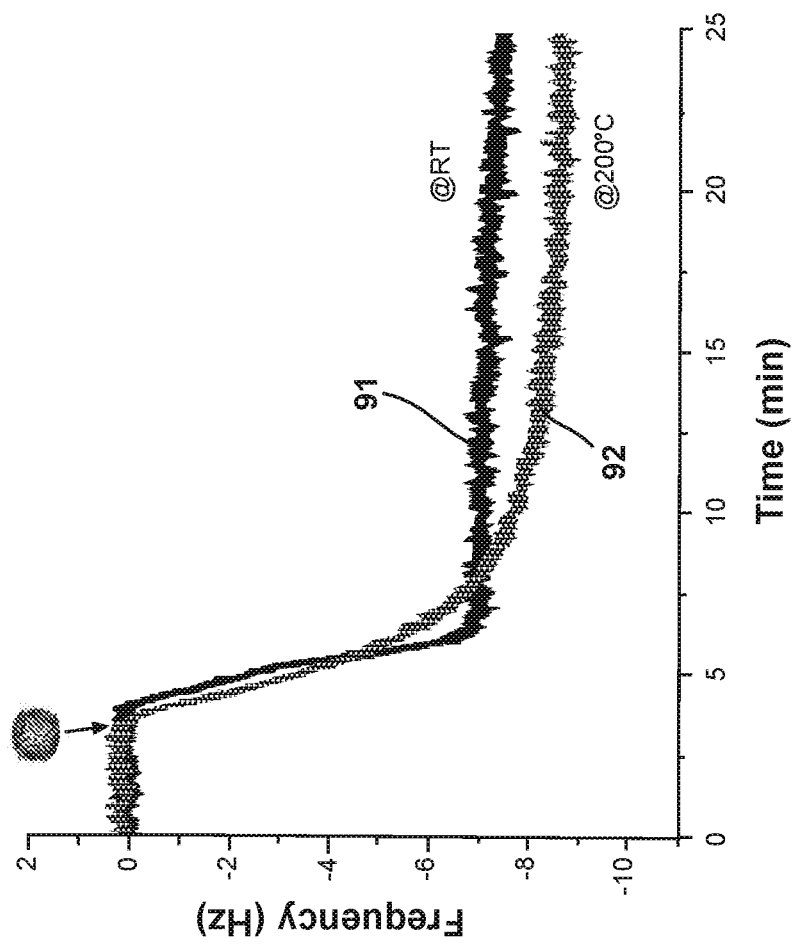
FIG. 7 depicts the antigen binding of an ionic liquid antibody at room temperature and at 200° C., according to an embodiment of the present invention.

FIG. 7 depicts the antigen binding of an ionic liquid antibody at room temperature (i.e. about 21-25° C.) 91 and at 200° C. 92 using a quartz crystal microbalance to measure mass of antigen adsorbed to an antibody immobilized quartz sensor. Binding is observed when the frequency decreases by more than about 2 Hz over time and a clear slope is observed vs. the initial baseline before antigen is added. FIG. 7 illustrates that an ionic liquid antibody solution can handle elevated temperatures and maintains functionality, as is depicted by the change in frequency response as temperature increases. As the temperature increases to 200° C., the antibody ionic liquid continues to exhibit binding activity similar to its performance at room temperature.

Numerous anions were identified as possibilities for making an antibody liquid salt. However, non-biological polymer anions may trigger an immune response if used in vivo. A few biological anions were discovered to be amenable to making protein ionic liquids, including DL-lactate, linolenate, phospholipids, fatty acids, and combinations thereof, which are biocompatible. These are presented only as examples and the invention is not intended to be limited solely to those biological anions. Any biologically-derived anion with a low melting point (e.g. between about 5-30° C.) that known in the art may be used. The same methodology is generally applicable to all antibodies and yields antibody ionic liquids which are stable and maintain efficacy up to 200° C., as illustrated in FIG. 7.

In one embodiment, creation of a water-free ultra-stable antibody ionic liquid, aqueous anti-hemoglobin antibodies produced in rabbits were cationized by addition of stoichiometric amounts of N,N-dimethyl-1,3-propanediamine in the presence of 1-ethyl-3-(3-dimethylaminopropyl) carbodiimide (EDC) coupling reagent; addition of succinimidyl iodoacetate (SIA) and 2-(dimethylamino) ethanethiol; and/or N-(p-maleimidophenyl) isocyanate (PMPI) and 2-(dimethylamino) ethanethiol. After cationization, the cationized antibodies were purified from excess coupling reagents by repeated dialysis in water using dialysis membranes with molecular weight cutoffs (MWCO) of 7000 g/mol. Purification is an optional step. Cationized antibodies were confirmed by a positive zeta potential value.

Next, the cationized antibodies were titrated with a corresponding non-toxic and bio-compatible counter anionic polymer of $C_9H_{19}C_6H_4$—($OCH_2CH_2$)$_{20}$O($CH_2$)$_3SO_3$ until positive charges on antibody became slightly negative by zeta potential measurements. This results in antibody cation/anion pairs which may be further processed to form an antibody ionic liquid.

The antibody cation/anion pair was dialyzed repeatedly in water to remove excess anionic polymer using MWCO 7000 dialysis membranes and lyophilized to remove all water, i.e. at least 95% or at least 99%.

Finally, lyophilized solid, e.g. powder, of the cationized anti-hemoglobin/anion pair was slowly, e.g. over a 20-minute period or more, heated to about 50° C. until a viscous clear liquid was generated. In one embodiment, the heating period is 30-90 minutes. In another embodiment, the cationized anti-hemoglobin pair is heated to 40-90° C. The anti-hemoglobin antibody ionic liquids were tested for antibody recognition of hemoglobin antigen using a dot blot assay on a nitrocellulose membrane and after heating at about 100° C. for 2 hours to test for temperature resistance. The antibody ionic liquid had retained its functionality, i.e. the functionality of its antibodies.

The resulting antibody ionic liquids are ultra-stable, possess long shelf-lives (i.e. greater than about 5 years), do not require refrigeration for storage/handling/use, do not have to adhere to a cold supply chain, are resistant to extreme temperatures (such as temperatures greater than about 100° C.), are non-toxic and biologically compatible, and can be easily reconstituted into water or a biological buffer for therapeutic use. By comparison, antibodies in aqueous solutions have limited shelf-lives even with controlled refrigeration, are extremely sensitive to increased temperatures, and quickly lose all biological recognition activity. In one embodiment, antibody ionic liquids provided by the disclosed method may reduce costs associated with refrigeration and may also eliminate the substantial weight burden of heavy refrigeration equipment.

In one embodiment, water-free antibody ionic liquids may also be prepared by the disclosed method with anti-hemoglobin antibodies, anti-horse spleen ferritin IgG antibodies, or blood-typing IgM Anti-A antibodies, stable single-chain antibodies from camelids, monoclonal Anti-Flag antibodies, monoclonal Anti-HRP2 to *Plasmodium falciparum*, polyclonal Anti-neuropeptide Y, and polyclonal Anti-human troponin, antibody fragments, or may contain combinations of multiple antibodies to create multi-recognition antibody liquids.

Ultra-stable antibody liquids may permit refrigeration-free handling, storage and antibody-based diagnostics. They are resistant to extreme temperatures, have long shelf lives (e.g. a 20-fold improvement of the prior art), reduce the cost/weight load of specialized refrigeration equipment, and are able to be transported to underdeveloped countries while maintaining efficacy.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method comprising:
    a) providing aqueous antibodies, wherein the antibodies are one of anti-hemoglobin antibodies;
    b) cationizing the aqueous antibodies by the addition of stoichiometric amounts of an excess of a positively-charged crosslinker in the presence of a coupling reagent, wherein the positively-charge crosslinker and coupling agent are selected from N,N-dimethyl-1,3-propanediamine in the presence of 1-ethyl-3-(3-dimethylaminopropyl) carbodiimide (EDC) coupling reagent succinimidyl iodoacetate (SIA) in the presence of 2-(dimethylamino) ethanethiol coupling reagent and/or the addition of N-(p-maleimidophenyl) isocyanate (PMPI) in the presence of 2-(dimethylamino) ethanethiol coupling reagent;
    c) titrating the cationized antibodies with a counter anionic polymer of poly(ethylene glycol) 4-nonylphenyl 3-sulfopropyl ether ($C_9H_{19}C_6H_4$—$(OCH_2CH_2)_{20}O(CH_2)_3SO_3$), forming an antibody cation/anion pair solution, until the antibody cation/anion pair solution becomes negative by zeta potential measurement, to create at least one antibody cation/anion pair in aqueous solution.

2. The method of claim 1, further comprising:
    d) lyophilizing the antibody cation/anion pair solution to remove all of the water, forming a lyophilized solid.

3. The method of claim 2, further comprising:
    e) heating the lyophilized solid until an antibody ionic liquid is generated.

4. The method of claim 2, further comprising:
    e) heating the lyophilized solid at about 27-50° C. until an antibody ionic liquid is generated.

5. The method of claim 1, further comprising:
purifying the cationized antibodies from excess coupling reagents by dialysis in water.

6. The method of claim 2, further comprising:
dialyzing the antibody cation/anion pair solution to remove excess anionic polymer with at least one membrane having a molecular weight cutoff of about 7000 g/mol.

7. The method of claim 2, further comprising:
dialyzing the antibody cation/anion pair solution to remove excess anionic polymer with at least one membrane having a molecular weight cutoff of between about 6000-15,000 g/mol.

8. The method of claim 1, further comprising:
confirming the cationizing of the aqueous antibodies by measuring a positive zeta potential value.

9. The method of claim 1, further comprising:
confirming the cationizing of the aqueous antibodies by measuring a zeta potential value between about 0 and +5 mV.

10. The method of claim 3, further comprising:
heating the antibody ionic liquid at about 100° C. for about 2 hours;
testing the antibody ionic liquid for antibody recognition of a corresponding antigen.

11. The method of claim 3, further comprising:
testing the antibody ionic liquid for antibody recognition of a corresponding antigen using a dot blot assay on a nitrocellulose membrane.

12. An ultra-stable ionic liquid comprising:
an antibody cation/anion pair comprising anti-hemoglobin antibodies.

* * * * *